(12) United States Patent
Schraermeyer

(10) Patent No.: US 7,488,749 B2
(45) Date of Patent: Feb. 10, 2009

(54) THERAPY OF DISEASES OF THE EYE, THE INNER EAR AND THE CENTRAL NERVOUS SYSTEM

(75) Inventor: Ulrich Schraermeyer, Tübingen (DE)

(73) Assignee: Cevec Pharmaceuticals GmbH, Cologne (DE)

( * ) Notice: Subject to any disclaimer, the term of this patent is extended or adjusted under 35 U.S.C. 154(b) by 313 days.

(21) Appl. No.: 10/505,030

(22) PCT Filed: Feb. 12, 2003

(86) PCT No.: PCT/DE03/00415

§ 371 (c)(1),
(2), (4) Date: Feb. 25, 2005

(87) PCT Pub. No.: WO03/070269

PCT Pub. Date: Aug. 28, 2003

(65) Prior Publication Data

US 2005/0142128 A1    Jun. 30, 2005

(30) Foreign Application Priority Data

Feb. 18, 2002 (DE) ................................ 102 06 723

(51) Int. Cl.
*A61K 31/405* (2006.01)
(52) U.S. Cl. ..................................... 514/415
(58) Field of Classification Search .................. 514/415; 548/469
See application file for complete search history.

(56) References Cited

U.S. PATENT DOCUMENTS

| 5,126,125 | A | * | 6/1992 | Pawelek | 424/62 |
| 5,686,084 | A |   | 11/1997 | Wenke et al. | 424/401 |
| 6,022,526 | A | * | 2/2000 | Woodburn et al. | 424/9.61 |

FOREIGN PATENT DOCUMENTS

| WO | WO 92/07580 | 5/1992 |
| WO | WO 00/10507 | 3/2000 |
| WO | WO 02/066620 | 8/2002 |

OTHER PUBLICATIONS

Novellino et al., Chem. Res. Toxicol, 1999, 12:985-992.*
ExPASy database. (1999).*
Barrenas and Lindgren, "The influence of eye colour on susceptibility to TTS in humans," *Br J Audiol*, 25(5):303-307, 1991.
Dorey et al., "Evidence of melanogenesis in porcine retinal pigment epithelial cells in-vitro," *Experimental Eye Research*, 50(1):1-10, 1990.
Ebadi et al., "The antioxidant properties of zinc and metallothionein," *Neurochem Int*, 29(2):159-166, 1996.
Frank et al., "Antioxidant enzymes in the macular retinal pigment epithelium of eyes with neovascular age-related macular degeneration," *Am J Ophthalmol*, 127:694-709, 1999.
GenBank Accession No. M27160. , 1996.
Orlow, "Melanosomes are specialized members of the lysosomal lineage of organelles," *J Invest Dermatology*, 105(1):3-7, 1995.
Peters et al., "Characteristics and functions of melanin in retinal pigment epithelium," *Der Ophthalmologe: Zeitschrift der Deutchen Ophthalmologischen Gesellschaft*, 98(12):1181-1185, 2001.
Rimbach et al.,"Zinc—update of an essential trace element," *Ernährungswiss*, 35(2):123-142, 1996.
Schraermeyer and Heimann, "Current understanding on the role of retinal pigment epithelium and its pigmentation," *Pigment Cell Res*, 12:219-236, 1999.
Schraermeyer et al., "Up-regulation of tyrosinase in adult mammalian retinal pigment epithelium by phagosytosis of rod outer segments," 15(Supp 9), XVIII International Pigment Cell Conference, Egmond aan Zee, Netherlands, Sep. 9-13, 2002.
Tate et al., "Zinc protects against oxidative damage in cultured human retinal pigment epithelial cells," *Free Radic Biol Med*, 26(5-6):704-713, 1999.

* cited by examiner

*Primary Examiner*—Rei-tsang Shiao
(74) *Attorney, Agent, or Firm*—Fulbright & Jaworski, LLP

(57) ABSTRACT

The present invention relates to 5,6-dihydroxyindole (DHI), 5,6-dihydroxyindole-2-carboxylic acid (DHICA) and/or 5-S-cysteinyldopa (CD) as medicaments, as well as their use, and the use of tyrosinase for the preparation of a medicament for prophylaxis or therapy of diseases induced by oxidative stress. Furthermore, the present invention relates to the use of gene therapy vectors comprising a tyrosinase gene. Further, the present invention relates to cells modified by a tyrosinase gene.

1 Claim, 1 Drawing Sheet

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Synthetic Primer

<400> SEQUENCE: 1
tagccagaag agaaacccac aaact                                    25

<210> SEQ ID NO 2

-continued

```
<211> LENGTH: 21
<212> TYPE: DNA
<213> ORGANISM: Artificial Sequence
<220> FEATURE:
<223> OTHER INFORMATION: Synthetic Primer

<400> SEQUENCE: 2
tccctcggtc gctgaacaag a                                      21

<210> SEQ ID NO 3
<211> LENGTH: 27
<212> TYPE: DNA
<213> ORGANISM: Artificial Sequence
<220> FEATURE:
<223> OTHER INFORMATION: Synthetic Primer

<400> SEQUENCE: 3
aactttgtga agctcatttc ctggtat                                27

<210> SEQ ID NO 4
<211> LENGTH: 19
<212> TYPE: DNA
<213> ORGANISM: Artificial Sequence
<220> FEATURE:
<223> OTHER INFORMATION: Synthetic Primer

<400> SEQUENCE: 4
ccttgctggg ctgggtggt                                         19
```

THERAPY OF DISEASES OF THE EYE, THE INNER EAR AND THE CENTRAL NERVOUS SYSTEM

This application claims priority to PCT/DE 03/00415, filed on Feb. 12, 2003, the entire contents of which are hereby incorporated by reference.

The present invention relates to 5,6-dihydroxyindole (DHI), 5,6-dihydroxyindole-2-carboxylic acid (DHICA) and/or 5-S-cysteinyldopa (CD) as medicaments, as well as their use, and the use of tyrosinase for the preparation of a medicament for prophylaxis or therapy of diseases induced by oxidative stress. Furthermore, the present invention relates to the use of gene therapy vectors comprising a tyrosinase gene. Further, the present invention relates to cells modified by a tyrosinase gene.

Tyrosinase is the most important enzyme in the synthesis of melanin, a pigment present in cells of the skin, the eye and the central nervous system.

Tyrosinase is an integral membranaceous glycoprotein consisting of 529 amino acids. The enzyme catalyses the hydroxylation of tyrosine to dihydroxyphenylalaline (DOPA) and subsequently its transformation into dopaquinone. In addition, melanin is produced by different intermediate steps (Stage-III-melanosome) which may proceed mostly spontaneously. 5,6-dihydroxyindole (DHI), 5,6-dihydroxyindole-2-carboxylic acid (DHICA), and 5-S-cysteinyldopa (CD) belong to these intermediate steps.

According to today's standard of knowledge the formation of melanin in mammalian retinal pigment epithelium, including the human eye, takes place only prenatally[2;5]. In humans the tyrosinase is active in retinal pigment epithelium only until about 6 weeks prior to the end of pregnancy, and is then not produced any more[4]. Melanin and tyrosinase, respectively, can be found in the eye in embryonically distinct tissues: in the uvea consisting of iris and chorioidea, as well as in the pigment epithelium of the retina (RPE), iris (IPE) and ciliary body. The only pigmented tissue which is claimed that no more melanin synthesis takes places there postnatally, is the RPE. This is based on work by Miyamoto and Fitzpatrick (1957)[4] in which it could be shown that no tyrosinase activity is to be found in postnatal RPE. According to the present state or the art, the enzyme itself has not been detected on protein level in RPE cells of adult mammals or humans, and no continuative studies have been performed either.

Whereas melanin predominantly represents a physical light shield in the skin, its functions in the eye are more complex[6]. A physical light shield is merely exhibited by the melanin of the iris (function as an aperture). Anatomically seen from the outside, the melanin in the retinal pigment epithelium (RPE) is located behind the sensitive photoreceptors of the retina (NH) which are to be protected. Here the pigment can reduce the scattered radiation by absorption, or protect tissues, such as endothelial cells of the choroid. Melanin has also a chemical protection effect. As a scavenger, melanin reduces the formation of lipid peroxidate ions which are toxic to tissues and which are formed in the RPE by means of a high concentration of oxygen, incidence of light from the outside and a pronounced activity in phagocytosis. The high concentration of oxygen results from an especially good blood circulation of the chorioidea which lies beneath it. Phagocytosis of secreted external segments of photoreceptors of the retina is one of the major tasks of the RPE and causes additional oxidative stress[1]. During phagocytosis superoxide is released extracellularly and intracellularly and which secondarily induces the formation of hydroxyl radicals and hydrogen peroxide[1].

Here, melanin is protective by reducing free radicals to molecular oxygen and hydrogen peroxide. Therefore, melanin has also protective effects in case of inflammation of the eye. Furthermore, melanin represent an important storage for zinc since it is able to bind heavy metals, such as zinc, medicaments and other cytotoxic substances and to store them. The RPE contains a high concentration of zinc which is for the most part bound to melanin[7]. Since zinc is a necessary co-factor for about 300 enzymes, such as the superoxide dismutase, the carbonic anhydrase, the retinal dehydrogenase, the collagenase and the catalase[8], a loss of melanin, e.g. in the case of AMD, may be associated with a loss of function of these enzymes. The enzymes mentioned before excerpt important functions especially in the eye. The activity of catalase is reduced in the eye of elderly people and especially in the case of AMD patients[9]. Thus, the cells are i.e. less protected against oxidative damages. Zinc which is reduced locally in the RPE and in the melanocytes of the choroid by the loss of melanin as well as systemically in the serum in the case of AMD, can also affect certain gene expressions. Zinc is required for various, i.e. anti-oxidatively operating, enzymes as a co-factor. A deficiency and complete absence, respectively, of melanin leads e.g. to the following diseases of the eye: Albinism, Hermansky-Pudlak syndrome (HPS), Chediak-Higashi syndrome (CHS), age-related macula degeneration (AMD). In the CNS, the Parkinson's disease correlates with a loss of melanin containing dopaminergic neurons of the substantia nigra. The content of melanin of the inner ear correlates with the sensitivity against oxidative stress caused by noise[10].

A causal therapy for Albinism, Hermansky-Pudlak syndrome and Chediak-Higashi syndrome is not known by now. In the case of albinos, the extreme photophobia is countered by the use of sun glasses.

A causal therapy of AMD is not known at present. Treatments with coagulation by argon laser can only be applied in the case of non-subfoveal CNV and they are just as the photodynamic therapy not able to prevent relapses.

The currently used standard therapies in the case of Parkinson's disease with L-DOPA show side effects and often lose their effectiveness after several years. Also dopamine agonists, MAO-inhibitors, amantadine and anticholinergics, show side effects or affect only single impacts of the disease.

The problem of the present invention is therefore to provide means for the prevention or therapy of diseases which are induced by oxidative stress in cells. A further problem is to provide means for the prevention or therapy of diseases of the eye, the inner ear and the central nervous system (CNS) which are correlated with a deficiency of the pigment melanin.

The problem is solved by the subject matter defined in the patent claims.

Figure 1:
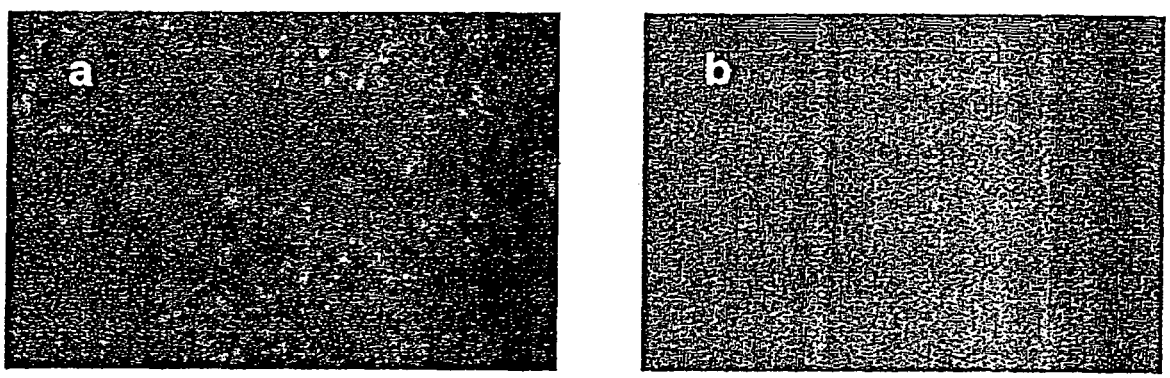
FIG. 1A shows human RPE cells in which the tyrosinase was inhibited by PTU after 15 feedings with membranes of visual cells. The cells show an intensive, golden auto-fluorescence which is specific for lipofuscin.
FIG. 1B shows schematically that the formation of lipofuscin and the auto-fluorescence associated therewith was hardly present in cells that were treated like the cells shown in FIG. 1A besides the fact that the tyrosinase was not inhibited by PTU.

The herein used term "tyrosinase" relates to a protein or polypeptide having the amino acid sequence which is specific for an enzyme with the biological activity of the tyrosinase as previously described. One example for a tyrosinase is the human melanogenic tyrosinase (EC 1.14.18.1). This tyrosinase is an integral membranaceous glycoprotein consisting of 529 amino acids (GenBank no. M27160). The tyrosinase belongs together with the human tyrosinase-related proteins I+II (TRP I+II) (GenBank no. for TRP I is AL138753 and for TRP II D17547), the Lysosome Associated Membrane Protein (Lamp; GenBank no. P11279) and gp100 (pmel 17; GenBank no. P40967) to one protein family. Therefore, the term tyrosinase includes proteins belonging to that protein family as well as potential modifications of the tyrosinase such as posttranslational modifications.

Further, the term tyrosinase comprises a nucleic acid having the sequence encoding one of the previously illustrated polypeptides. Thereby, not only the hitherto known sequences but also the sequences of derivatives, i.e. substitutions, additions, deletions, insertions, inversions, and also the sequences exhibiting fragments and modifications are encompassed by said term. The nucleic acid comprises not only the respective cDNA but may furthermore contain the genomic locus including the introns, regulatory elements, etc. A nucleic acid is comprised by the term "tyrosinase" if the protein or polypeptide encoded by it exhibits the biological activity of the tyrosinase.

The herein used term "vector" or "gene transfer vector" relates to natural occurring or artificially generated constructs and organisms for the uptake, propagation, expression or transfer of nucleic acids in cells. Examples for gene transfer vectors are viruses, such as adenoviruses, adeno-associated viruses, lenti viruses, retro viruses, pox viruses, alpha viruses, baculoviruses, rabies viruses or herpes viruses. The gene transfer vectors are capable of autonomous replication inside a cell or of integration into the genome of the cells. The gene transfer vector is constructed such that it contains at least one desired therapeutic polynucleotide to be replicated and/or expressed. Furthermore, the gene transfer vectors may contain further polynucleotides such as a selection marker.

Oxidative stress is e.g. triggered by phagocytosis. Surprisingly, the inventor found that the tyrosinase and its metabolites such as 5,6-dihydroxyindole (DHI), 5,6-dihydroxyindole-2-carboxylic acid (DHICA) and/or 5-S-cysteinyldopa (CD) may offer a protective function at time points of increased exposure to reactive oxygen species and may protect cells and tissues against oxidative stress.

Oxidative stress means the formation of reactive oxygen species in cells or tissues. These oxygen species are superoxide anion, hydroxyl radical and $H_2O_2$. These species are formed e.g. during the reactions of the respiratory chain in the mitochondria of each cell. The risk of a cellular damage increases if the tissue exhibits a high metabolic activity (e.g. brain) or is intensely exposed to light (eye, skin). The oxygen species (superoxide anion, $H_2O_2$) are eliminated by anti-oxidative enzymes (superoxide dismutase, catalase, glutathion peroxidase and others). However, if this elimination is not completely accomplished hydroxyl radical is formed which causes severe cell damages and cell death: Cellular ageing and ageing of whole organisms are ascribed to the damages caused by reactive oxygen species. A well known cellular damage triggered by oxidative stress is the lipid peroxidation. Oxidative stress causes neurological degenerative diseases (e.g. Parkinson's disease, age-related macula degeneration, Alzheimer's disease, degenerative diseases of the inner ear) and cardiovascular diseases (e.g. heart attack, atherosclerosis) but also the formation of tumours (e.g. melanoma).

Lipofuscin is a brownish-yellowish, electron-dense, autofluorescent pigment which is accumulated in the lysosomes of postmitotic cells such as nerve cells, myocardial cells, pigment epithelium cells of the eyes and the skin cells, especially if exposed to the oxidative stress. Oxidative stress causes lipid peroxidation. Said peroxidative lipids cannot be completely degraded and are in part transformed into lipofuscin. Lipofuscin has a considerable pathological impact especially in the retinal pigment epithelium and is presumable caused by the incomplete degradation of outer segments of visual cells. These are especially easily transformed into lipofuscin if reactive oxygen species are present, because of their high content of unsaturated fatty acids. By means of the content of lipofuscin the age of a cell can be concluded. The spots of lipofuscin in the skin of ageing humans are referred to as ageing pigment. The exact chemical composition of lipofuscin is not known. One component consists of ethanolamine.

Drusen are deposits of residual cellular material of unknown origin under the pigment layer between or within the Bruch's layer and the RPE. It is possible that they are formed as a consequence of a dysfunction of phagocytosis and degradation of retinal pigment cells; and it is assured that in the case of complex diseases of the retinal, pigment epithelium, choroid complex, including AMD in humans, drusen play a role. Funduscopically so called soft drusen having a diffuse boundary or hard drusen having sharp boarders are discriminated. If drusen are formed in the region of the macula, this is associated with a pronounced loss of sight.

Therefore, one aspect of the present invention is to provide 5,6-dihydroxyindole (DHI), 5,6-dihydroxyindole-2-carboxylic acid (DHICA) and/or 5-S-cysteinyldopa (CD) as medicaments. A further aspect of the present invention is the use of tyrosinase, 5,6-dihydroxyindole (DHI), 5,6-dihydroxyindole-2-carboxylic acid (DHICA) and/or 5-S-cysteinyldopa (CD) for the preparation of a medicament for the treatment or prophylaxis of diseases induced by oxidative stress. In particular, the medicaments are used for the treatment of drusen or of an increased content of lipofuscin or for prophylaxis of the formation of drusen or of the formation of lipofuscin. Preferably, the diseases comprise diseases of the eye, in particular age-related macula degeneration (AMD), albinism, Hermansky-Pudlak syndrome (HPS), Chediak-Higashi syndrome (CHS), choroidal and retinal neovascularisation, diabetic retinopathy and retinopathy of the prematury, degenerative diseases of the inner ear (presbycusis) and diseases of the CNS, in particular Parkinson's disease.

However, the therapeutic may not only be administered in terms of a chemical substance (5,6-dihydroxyindole (DHI), 5,6-dihydroxyindole-2-carboxylic acid (DHICA) and 5-S-cysteinyldopa (CD)) or in form of a protein or a polypeptide (tyrosinase) but also in terms of a nucleic acid molecule encoding that polypeptide. The nucleic acid molecule may be introduced into the target cells by means of gene transfer vectors.

The expression of the tyrosinase gene in the gene transfer vectors is controlled by promoters. Viral or non-viral promoters which are constitutively, tissue specifically or controllably active may be used for the expression. For example the SV40 or cytomegalovirus promoter can be used for the constitutive expression of a gene. The use of the tissue specific promoter allows the tissue specific expression, e.g. in melanocytes, IPE or RPE cells. An example for such a tissue specific promoter is the transthyretin promoter that has a good activity in RPE and IPE cells. The gene expression may be controlled quantitatively and qualitatively by the use of a controllable expression system. One example for a controllable gene expression system is the tetracycline dependent gene expression system or the RU 486 system.

Both viral and non-viral vectors may be used for the gene transfer into the target cells. Examples for viral vectors are adenoviral vectors, AAV vectors, retroviral vectors and lentiviral vectors. Examples for non-viral vectors are liposomes and cationic lipids. Furthermore, any kind of vector or carrier can be used which is able to introduce the nucleic acid into the target cell.

The vectors may be injected e.g. subretinally or into the choroid for the treatment of diseases of the eye. For the treatment of diseases of the CNS, vectors may be injected e.g. in the substantia nigra, the putamen or striatum. Preferred target cells are stromal bone marrow cells, fibrocytes, melanocytes, retinal pigment epithelium cells, pigment epithelium cells of the iris and of the ciliary body, pericytes, endothelial cells, dopaminergic neurons, neurons, Schwann cells, astrocytes, microglia, Müller cells or neuronal gliocytes.

In a preferred embodiment of the present invention the formation of tyrosinase is induced by genetic modifications of RPE cells with adenoviral vectors thereby protecting the retinal tissue against light induced oxidative stress and, furthermore, reducing the formation of lipofuscin and a neovascularisation. For example, in the case of patients with AMD up to 60% of the cellular volume of RPE cells are filled with lipofuscin which interferes with the function of the cells. Moreover, the tyrosinase can be used for the elimination of reactive oxygen species such as $H_2O_2$, superoxide anion and hydroxyl radicals in lysosomes.

In a further preferred embodiment of the present invention the formation of tyrosinase is induces by genetic modifications of cells of the CNS with adenoviral vectors which leads to the increase of synthesis of dopamine and to the binding of iron and elimination of reactive oxygen species by the metabolites of the tyrosinase. Furthermore, thereby the lysosomal activity in neurons is activated.

The use of the tyrosinase is preferred in case of pigment deficiency diseases and hypopigmention of all kinds, such as vitiligo, allopecia, graying of hair, achromatosis, piebaldism, albinism, retinopathy of the prematury (ROP), retinitis pigmentosa, diabetic retinopathy, age-related macula degeneration, Parkinson's disease, Hermansky-Pudlak syndrome, Chediak-Higashi syndrome.

Furthermore, one aspect of the present invention resides in the genetic modification of cells which are then administered to the patient. Thereby, the cells may be transduced by the gene transfer vectors previously described. Furthermore, the cells may be transfected by the nucleic acid molecule comprising the tyrosinase gene.

In the case of diseases of the eye, for example cells originating from the adrenal cortex, pigment epithelial cells of the iris, retinal pigment epithelium cells, stem cells from the bone marrow, sertoli cells from the gonads, glomus cells from the carotids, fibroblasts or astrocytes, neuronal stem cells or other cells of the body may protect against oxidative damages in the choroid (e.g. at endothelial cells) or the retina by genetic alteration with the tyrosinase gene. The herein mentioned cells may be obtained both from foetuses and autologously. At the same time, the lysosomal activity of the cells may be increased thereby reducing the formation of lipofuscin. The formation of nitrogen monoxide (NO) may be activated by the formation of DOPA which exhibits a positive effect on the flow of the blood in the choroid. These mechanisms prevent neovascularisation in the case of diseases of the eyes, such as age-related macula degeneration, diabetic retinopathy or retinopathy of the prematury.

For instance, foetal cells obtained from brains of human foetuses, e.g. from the ventral mid-brain, or dopaminergic neurons may be used. Furthermore, various different cell types, among them also non-neuronal cells e.g. cells from the adrenal cortex, pigment epithelium cells of the iris, stem cells from the bone marrow, sertoli cells from the gonads, glomus cells from the carotids, fibroblasts or astrocytes or neuronal stem cells e.g. from brains of adult vertebrates, may be used.

In the case of Parkinson's disease, transplanted cells which are modified with the tyrosinase gene, may develop neural protective effects by the antioxidative effect of their melanin granula.

In a further preferred embodiment of the invention, dopaminergic neurons or other neuronal cells of the CNS are to be transduced with the tyrosinase gene in the case of patients with Parkinson's disease in order to at the one hand activate the formation of melanin and/or to on the other hand enhance the production of dopamine. Preferably, the used cells are autologous cells.

A further aspect of the present invention is to provide 5,6-dihydroxyindole (DHI), 5,6-dihydroxyindole-2-carboxylic acid (DHICA) and/or 5-S-cysteinyldopa (CD) as medicaments. The substances may not only be administered as chemical substances but are also produced during the administration of tyrosinase polypeptides or during the genetherapeutic modification of cells with the tyrosinase gene. Due to the expression of tyrosinase the substances according to the invention are formed as intermediate steps of the melanin synthesis and may diffuse e.g. from the modified cells of the RPE into the choroid or retina, or from the modified CNS cells into the CNS and actively exhibit the described protective functions.

A further aspect of the present invention is to provide a combinatory composition consisting on the one hand of 5,6-dihydroxyindole (DHI), 5,6-dihydroxyindole-2-carboxylic acid (DHICA), 5-S-cysteinyldopa (CD) and/or tyrosinase and on the other hand of zinc as medicaments. In particular, the invention relates to the provision of the combinatory composition for the treatment of age-related macula degeneration, diabetic retinopathy, Parkinson's disease, for the reduction of the neoplasm of blood vessels, of lipofuscin and of drusen and of degenerative diseases of the inner ear (presbycusis).

Thereby zinc may be administered simultaneously or after the other substances used in the combinatory composition. Preferably, the concentration of melanin is first increased in the cells affected by the disease, e.g. the choroid, the substantia nigra or in RPE by administration of the gene transfer vectors previously described. Subsequently, the concentration of zinc is increased in the artificially pigmented tissues by the substitution with zinc, thereby improving the anti-oxidative protective effects of the melanin and its metabolites[11]. The administration of zinc may occur orally. The blood vessels of the choroid and neuronal cells in the CNS cells may be protected by reducing the oxidative stress. The neoplasm of blood vessels, the formation of lipofuscin and drusen may be reduced by the combination therapy according to the present invention.

The following examples illustrate the invention.

EXAMPLE 1

Induction of Tyrosinase by Phagocytosis In Vitro

Human retinal pigment epithelium cells were isolated 2 hours post mortem from eyes of organ donors by incubation in 0.2% trypsin solution with 0.5 mM EDTA (if not indicated differently the reagents are from Sigma, Deisenhofen, Germany) for 30 minutes. The cells were centrifuged and cultivated in 24-well-plates (Nunc, Mainz, Germany) in Dulbeccos modified Eagle Medium with 15% foetal calf serum, 50 µg/ml gentamycin and 2.5 µg/ml amphotericin. The cells remain in primary culture (P0) for 3 weeks until confluence.

Subsequent passaging was performed by trypsination of the cells in the respective time intervals. For the feeding with membranes of visual cells, cells originating from 3 different donors (passage 3, 6 and 16) were used.

EXAMPLE 2

Isolation of Membranes of Visual Cells

Isolated retinas from bovine eyes were vigorously shaken for 2 minutes in KCl-buffer (0.3 M KCl, 10 mM Hepes, 0.5 mM $CaCl_2$, 1 mM $MgCl_2$ and 48% sucrose) at pH 7 and then centrifuged at 2000 rpm in a table centrifuge (Type ZJ 1, Christ, Germany) for 5 minutes. The supernatant was filtrated to a gauze finger stall and diluted with KCl-buffer (1:1) and re-centrifuged at 2500 rpm for 10 minutes. The isolated outer segments of the rods were washed twice by centrifugation in 10 mM Tris-buffer (Trisma base) at pH 4, pelleted and frozen at minus 80° C. prior to use.

EXAMPLE 3

Phagocytosis of Membranes of Visual Cells

RPE cells which were adapted to the culturing conditions for 2 weeks were overlaid with about $2 \times 10^6$ outer segments of rods. After 4 hours the non-phagocytosed membranes of visual cells were washed away and replaced by fresh medium. After 0, 5, 20 and 40 hours, the cells were fixed in 4% paraformaldehyde or dissolved in Trireagent and used for the different analyses. Unfed cells served as controls.

EXAMPLE 4

Histochemical Detection of Tyrosinase with DOPA

A portion of the cells was fixed without feeding and 20 hours after incubation with membranes of visual cells, respectively, in 2% glutaraldehyde in 100 mM sodium cacodylate buffer for 2 hours (pH 6.8) and incubated with 5 mM L-dihydroxyphenylalanin (L-DOPA) for 1 hour. Subsequently, these cells were embedded for electron microscopy according to routine method, ultra-thinly cut and analysed in a Zeiss EM 9 (Oberkochem, Germany) electron microscope.

In fed cells electron dense golgi apparatus and numerous cytoplasmatic vesicles were present. Occasionally, phagosomes were detectable which have become electron dense due to the DOPA reaction. In unfed cells electron dense material due to the DOPA reaction was not found.

EXAMPLE 5

Detection of Tyrosinase by Immuno Histochemistry of Cultivated Cells

Cells which were cultivated on microscope slides were fixed in 4% paraformaldehyde in 0.1 M PBS for 15 minutes, washed in 0.05 M TBS (trishydroxymethylaminomethane), permeabilised in 0.25% Triton (Serva) and blocked with 5% BSA (bovine serum albumin) for 40 minutes. The cells were incubated with the first anti-tyrosinase monoclonal antibody (Chemicon International Inc.) (1:150) over night. The incubation with the secondary Cy2 conjugated antibody (AffiniPure Goat Anti-Mouse IgG, Dianova) (1:100) took 1 hour. In a further step, the preparations were incubated with anti-rhodopsin antibodies (Leinco Techn Instr., diluted 1:50) over night. The primary antibodies were visualised by anti-mouse IgG coupled to the fluorescence dye Cy3 (Rockland, Gilbertsville, Pa., USA). These cells were analysed under the fluorescence microscope (Axiophot, Zeiss, Oberkochem, Germany). 6 visual fields each with about 50 cells were analysed.

|  | Cells with tyrosinase containing vesicles in % | Cells with tyrosinase and rhodopsin containing vesicles in % |
|---|---|---|
| 24 hours after incubation with ROS | 8 ± 10.2    n = 6 | 0.5 ± 0.6    n = 6 |
| without ROS | 1 ± 1.3    n = 6 | 0 ± 0    n = 6 |
| Student's t-test | p = 0.00019 | |

EXAMPLE 6

Detection of Tyrosinase in Retinal Pigment Epithelium Cells of Rats

Eyes of Long Evans-rats held in a 12 hours light/dark light cycle (light on at 7 o'clock in the morning) were removed at 8 o'clock and 10 o'clock. The eyes were enucleated, broached in height of the limbus by a scalpel and fixed in 4% paraformaldehyde over night. On the next day, the front part of the eyes was cut-off as far as short behind the ora serrata by an circumferential cut. The remaining eye cup was divided into quadrants by 4 radial cuts and the retinas were removed. Quadrants consisting of a pigment epithelium, choroidea and sclera containing laser scars, were incubated 4×10 minutes in Tris-buffer (TBS) and then for 10 minutes in 0.5 M $NH_4Cl$ and 0.25% Triton (Serva, Heidelberg, Germany). After two further rinsings, the preparations were incubated with 5% BSA (albumin, bovine fraction). The flatmounts were incubated with anti-rhodopsin and anti-tyrosinase antibodies as described for the cultivated cells. As control, the cells were incubated with monoclonal antibodies against tyrosine hydroxylase from rat phaeochromocytoma (Boehringer, Mannheim, Germany) diluted 1:500. The "Flatmount-preparations" were analysed under the fluorescence microscope (Axiophot, Zeiss, Oberkochem, Germany). The preparations were separately photographed with the respective filter sets for Cy2 and Cy3 with a digital camera and overlaid using Openlab Software (Improvision, UK). Cells containing the tyrosinase, tyrosinase and rhodopsin positive vesicles were counted. All cells were negative for tyrosine hydroxylase. The number of positive cells is depicted in the following table. In each case, visual fields with on average 250 cells were analysed.

|  | Cells with tyrosinase containing vesicles in % | Cells with tyrosinase and rhodopsin containing vesicles in % |
|---|---|---|
| 8 o'clock | 0.6 ± 0.3    n = 23 | 0.3 ± 0.3    n = 11 |
| 10 o'clock | 1.2 ± 3.3    n = 30 | 0.2 ± 0.4    n = 16 |
| Student's t-test | p = 0.01 | |

EXAMPLE 7

Inhibition of the Tyrosinase Enhances the Formation of Lipofuscin in RPE Cells Human RPE cells adapted on the culture conditions for 2 weeks were divided into 3 experimental groups.
1.) 1 mM phenylthiourea (phenylthiourea PTU, Sigma, Deisenhofen, Germany) and inhibitor of the tyrosinase, was added into the culture medium of the cells.
2.) The cells in group 2 were cultivated without PTU as a control.
3.) The cells in group 3 were cultivated as in group 1 with PTU but not fed.

The cells in group 1+2 were overlaid with about $2 \times 10^6$ outer segments of rods. The concentration of PTU remained constant all the time. After 4 hours the non-phagocytosed membranes of visual cells were washed away and replaced by fresh medium. This was performed on 15 successive days. After this, the cells were looked at under the fluorescence microscope (Axiovert, Zeiss, Oberkochem, Germany) with filters specific for the auto-fluorescence of the lipofuscein (excitation 360 nm, emission 540 nm, Feuerbacher Analysentechnik, Tübingen, Germany) and were photographed with a digital camera and saved using Openlab Software (Improvision, UK).

RPE cells of group 1 in which the tyrosinase was inhibited by PTU showed an intensive, golden auto-fluorescence specific for lipofuscin (FIG. 1a) after feeding with membranes of visual cells for 15 days. That auto-fluorescence was in cells of group 2 only weekly pronounced (FIG. 1b). Cells which were only incubated with PTU (group 3) showed no auto-fluorescence. Tyrosinase inhibits the formation of lipofuscin in the retinal pigment epithelium.

EXAMPLE 8

Western Blot

Western bloting was performed with cultivated human RPE cells prior to and 5 and 40 hours after feeding with membranes of visual cells. Two melanoma cell lines were used along for the control of the tyrosinase expression. The protein samples (75 μg each) were either blotted on a NC-membrane (M1) or a PVDF-membrane (polyvinylidine difluoride membrane, M2). M1 was washed in TBS, stained with India Ink and washed again. M2 was washed with aqua dest., stained with Ponceau S and washed again. The reaction was stopped with 5% BLOT-Quick Blocker (Chemicon) and TBS-T (0.05% Tween-20, 1×TBS) for 1 hour at room temperature. The samples were incubated with 20 ml mouse anti-tyrosinase monoclononal antibody (DUNN/Chemicon MS 800) diluted 1:500 in TBS-T at 4° C. over night. After washing with 20 ml TBS the secondary antibody HRP-anti-mouse IgG (Horse radish peroxidase, dilution 1:6000 in TBS-T) was incubated for 2 hours at room temperature and subsequently washed away. All samples were incubated with monoclonal antibodies against human β-actin (Sigma, Deisenhofen, Germany) diluted 1:800 over night. Peroxidase was visualised with LumiLight 1:1 vol. Luminol/Enhancer. The peroxidase solution was incubated in a clingwrap.

A strong positive band with the molecular weight of 75 kD showed up in the melanoma cells. The same band was very weakly detectable in unfed RPE cells and doubled by thickness 5 hours after feeding returning to its initial value prior to feeding after 40 hours after feeding. The intensity of the bands for β-actin remained constant in all samples.

The results show an increase of the tyrosinase expression on protein level as a consequence of the incubation with membranes of the visual cells.

EXAMPLE 9

Increase of the Intracellular Zinc Concentration in Pigmented Tissue

Two albino (Wistar) rats and two pigmented (Long Evans) rats were injected intraperitoneally with 40 mg/kg body weight $ZnCl_2$. After 24 hours the chorioidea-RPE-complex was isolated from retina and sclera. Respective samples from untreated animals served as controls. The samples were weight directly into leak-proof PFA vessels (Savillex) (Microbalance Sartorius MC21S) and cracked by using ultrasound homogenisation for 24 hours at 30° C. with $HNO_3$—$H_2O_2$ (suprapur grade reagents; Merck). After careful evaporation, the remains were solved in 2% $HNO_3$ for 5 hours at 50° C. This solution was subsequently transferred to a 10 ml volumetric flask. The final clear solution contained 10 ng rhodamin (Rh)/ml and was refilled with 2% $HNO_3$. The detection of zinc was performed by inductively coupled plasma mass spectrometry (ICP-MS, ELAN 6000 Perkin-Elmer/Sciex) and by using Rh as internal standard and a calibration with chemical reagents having the highest purity grade.

The zinc concentration of the chorioidea-RPE-complex was 5.1 μg/g in the case of untreated albino rats, 74 μg/g in the case of pigmented rats and did not increase in the tissue of albinos (6.5 μg/g), however, it increased by the factor 1.6 in pigmented rats (125 μg/g) 24 hours after injection of zinc. In pigmented rats the final concentration of zinc after injection was 19 times higher than in the albinos which were treated accordingly.

EXAMPLE 10

Increase of the Intracellular Zinc Concentration and of Further Elements in Artificially Pigmented Tissue 0.008 mg melanin from squid (Sepia officinalis, Sigma) dissolved in 1 μl physiological saline solution was subretinally injected in 8 eyes of albino (Wistar) rats. After 3 days the animals were injected intraperitoneally with 40 mg/kg body weight $ZnCl_2$. Respective samples of untreated albinos served as controls (4 eyes). After 24 hours the artificially pigmented chorioidea-RPE-complexes were isolated from retina and sclera. The samples were directly weight (Microbalance Sartorius MC21S) into 7 ml leak-proof PFA-vessels (Savillex) and cracked (24 h/30° C. using ultrasound homogenisation) with $HNO_3$—$H_2O_2$ (suprapur grade reagents, Merck). The detection of zinc was performed by using inductively coupled plasma mass spectrometry as described previously.

The zinc concentration of the chorioidea-RPE-complex was 49.6 μg/g in artificially pigmented tissues and 5.1 μg/g without melanin injection. This corresponds to an increase of the zinc concentration by the factor 9.7 in comparison to tissue samples from untreated albino rats 24 hours after the injection of zinc. Also the concentration of the elements Ca, Mn, Fe, Co, Ni, Cu, and Cd was significantly increased by the injection of melanin towards the values which are normal in case of pigmented animals (see table below).

TABLE

Concentration in µg/g wet weight RPE-chorioidea-complex

| | Ca | Mn | Fe | Co | Ni | Cu | Zn | Cd |
|---|---|---|---|---|---|---|---|---|
| albino rat | 37 | 0.11 | 7.7 | 0.01 | 0.33 | 0.77 | 5.1 | 0.01 |
| albino rat + melanin injection | 634 | 0.65 | 97 | 0.08 | 1 | 5.08 | 49.6 | 0.02 |
| pigmented rat | 2823 | 1.56 | 94 | 0.13 | 4 | 14.1 | 74 | 0.07 |

These results show that the concentration of trace elements in the tissue may be increased by an artificial increase of the melanin concentration. This increase may on the one hand support the physiological functions of the cells, on the other hand also toxic elements (Fe, Cd) may be closely bound by melanin thereby protecting the cytoplasm of the cells against the damaging effects of these elements

EXAMPLE 11

Increase of the mRNA for Catalase by Injection of Zinc

Albino (Wistar) rats and pigmented (Long Evans) rats were injected intraperitoneally with 40 mg/kg body weight $ZnCl_2$. After 6 and 24 hours the chorioidea-RPE-complex was isolated from the retina and sclera. The amount of catalase mRNA expression in the chorioidea-RPE-complex was quantified by real time RT-PCR with the SYBR Green I reaction system using an iCycler (Bio-Rad Laboratories, Hercules, Calif.). PCR primer (catalase: upper primer: TAG CCA GAA GAG AAA CCC ACA AAC T (SEQ ID NO:1) and lower primer: TCC CTC GGT CGC TGA ACA AGA (SEQ ID NO:2); GAPDH: upper primer: AAC TTT GTG AAG CTC ATT TCC TGG TAT (SEQ ID NO:3) and lower primer: CCT TGC TGG GCT GGG TGG T (SEQ ID NO:4)) were selected using the primer analysis software OLIGO®4.1 (National Biosciences, Plymoth, Minn., USA) that the primer specific melting temperature was between 58 and 60° C. The length of the fragments was 116 bp (catalase) and 123 bp (GAPDH). The analysis of the gene expression was repeated three times. 25 ng cDNA were subjected to an amplification using reaction buffer with Tris-HCl, KCl and $(NH_4)_2SO_4$, 1.5 mM $MgCl_2$, 0.2 mM of each dNTP, 0.2 µM of each primer, 0.1× SYBR Green I (Molecular Probes Europe, Leiden, Netherlands) and 1.2 U HotStart DNA polymerase (Qiagen, Hilden, Germany) in a volume of 50 µl per sample. Following PCR parameters were used: initiation at 95° C. for 15 min., then 40 cycles at 95° C. for 20 sec., 55° C. for 20 sec. and 72° C. for 20 sec. To check the specificity of the amplification the PCR products were subjected to a melting point analysis. The quantification data were calculated using the iCycler iQ System Software (Bio-Rad Laboratories, Hercules, Calif.). After subtraction of the PCR base line by the software, the linear logarithmic portion of the fluorescence was plotted versus the number of cycles to determine the cycle number (threshold cycle, $C_T$) at which the threshold fluorescence for catalase and GAPDH as a reference was exceeded. Since the amplification effectivity of target and reference gene was approximately the same (delta $C_T<0.15$) the comparative $C_T$ method was used for the quantification of the catalase in comparison GAPDH.

The concentration of the mRNA for catalase without zinc injection was exactly the same in chorioidea-RPE-complexes of albinos and pigmented animals. Six hours after zinc injection the mRNA for catalase was increased by the factor 12. After 24 hours this difference disappeared and the amount of mRNA for catalase was again as high as without zinc injection. These results show for the first time that melanin, potentially by means of an increased intracellular uptake, supports the gene expression for catalase which is induced by zinc.

EXAMPLE 12

Melanin Protects Against Retina Degeneration Caused by a Zinc Deficiency

Five months old albino (Wistar) rats and pigmented (Long Evans) rats were fed exclusively a zinc depleted diet for 42 days (C1040, Altromin GmbH, Lage, Germany, Charge No. 436). The eyes were enucleated and embedded in plastic for the electron microscopy according to routine methods. The still remaining photoreceptors were counted in 4 eyes per group using semi-thin sections. Per eye, the maximum number of photoreceptor rows was counted at 3 different locations. The results were analysed statistically using the Student's t-test.

In both experimental groups a loss of photoreceptors could be observed. The mean values from 12 measurements of the maximally present photoreceptor nuclei were 5.3±1 in the case of albino rats and 9.6±0.6 in the case of pigmented rats. The difference is highly significant (p=0.00001). The outer segments of the photoreceptors were about twice as long in the case of pigmented rats as in the case of albinos. These results show for the first time that melanin may protect against degeneration of the retina caused by a zinc deficiency. Probably the zinc stored in the melanosomes could be released so that the zinc dependent cell functions functioned better and longer in the case of pigmented animals than in the case of the albinos.

EXAMPLE 13

Zinc in Combination with Melanin Protect Cells Against Lethal UVA Radiation 30.000 human amelanotic retinal pigment epithelium cells ARPE-19 (American Type culture Collections, Manassas, Va., USA) were cultivated in a mixture of DMEM and F12 Medium (PAA Laboratories, Linz, Austria) with 10% foetal calf serum, gentamycin and amphotericin and were incubated with 1 mg/ml melanin from squids (Sepia officinalis, Sigma). After 4 hours, the non-phagocytosed melanin was thoroughly washed away. After 24 hours the artificially pigmented cells were incubated with 100 or 200 µmol $ZnCl_2$ for 2 hours. Three days later, the cells were irradiated using a HRL, 125 W, lamp (Radium, Germany) for 1 hour. The UVA light portion was 18 mW/cm² at the surface of the cell culture liquid and was measured using a RM-12 UV radiometer (Dr. Gröbel, UV Elektronik, Ettlingen, Germany). Cells without melanin and zinc treatment with and without irradiation served as controls. After 2 further days, the number of surviving cells was counted in a Thoma-chamber.

In the following table the mean values of surviving cells from 3 independent experiments are indicated. The number of surviving cells after irradiation without melanin and/or zinc treatment was statistically compared with the number of surviving cells with treatment. That is were the p-value results from. Each treatment has significantly increased the survival rate of the cells. The best protective effect had a combination of melanin administration and incubation with 100 µmol zinc. The number of surviving cells war increased by the factor 7.4 in comparison to untreated cells. This shows that a combination of intracellular melanin increase and zinc substitution significantly protects retinal pigment epithelium cells against UVA phototoxicity (see table below).

| without irradiation, without Zn, without melanin | with irradiation, without Zn, without melanin | with radiation, with 100 μmol Zn | with irradiation, with 200 μmol Zn | with irradiation, with 100 μmol Zn, with melanin | with irradiation, with 200 μmol Zn, with melanin |
|---|---|---|---|---|---|
| 335000 ± 15000 | 11666 ± 2886 | 33333 ± 11547<br>p = 0.03 | 41666 ± 16072<br>p = 0.03 | 86666 ± 20207<br>p = 0.003 | 70000 ± 25000<br>p = 0.015 |

EXAMPLE 14

Zinc in Combination with Melanin Reduces the Formation of $H_2O_2$ in Retinal Pigment Epithelium Cells after UVA Irradiation 30.000 human amelanotic retinal pigment epithelium cells ARPE-19 (American Type culture Collections, Manassas, Va., USA) were cultivated in a mixture of DMEM and F12 Medium (PAA Laboratories, Linz, Austria) with 10% foetal calf serum, gentamycin and amphotericin and were incubated with 1 mg/ml melanin from squids (Sepia officinalis, Sigma). After 4 hours the non-phagocytosed melanin was thoroughly washed away. After 24 hours the artificially pigmented cells were incubated with 100 or 200 μmol $ZnCl_2$ for 2 hours. The in such a way treated and untreated cells were incubated with 60 μM 2',7'-dichlorofluorescin diacetate (Sigma, Deisenhofen, Germany) which is fluorescent if it is oxidised by $H_2O_2$, and irradiated using a HRL, 125 W, lamp (Radium, Germany) for 15 minutes. The UVA light portion was 18 mW/cm² at the surface of the cell culture liquid and was measured using a RM-12 UV radiometer (Dr. Gröbel, UV Elektronik, Ettlingen, Germany). Cells without melanin and zinc treatment with and without irradiation served as controls. The fluorescence intensity was measured using a CytoFluor Multi-well Plate-Reader (PerSeptive Biosystems, Wiesbaden, Germany).

In the following table the fluorescence intensities are indicated in percent whereas a lesser fluorescence indicates a lesser formation of $H_2O_2$. The best protective effect exhibited a combination of melanin administration and incubation with 100 μmol zinc. The maximum fluorescence in untreated cells was set as 100%. The fluorescence intensity was reduced by 60% in comparison to untreated cells (see table below). This shows that a combination of intracellular melanin increase and zinc substitution protects retinal pigment epithelium cells against the formation of $H_2O_2$ which is induced by UVA light (see table below).

| Fluorescence intensity with irradiation, without Zn, without melanin | Fluorescence intensity with irradiation, with melanin and 100 μmol Zn | Fluorescence intensity with irradiation, with melanin, without Zn |
|---|---|---|
| 100% | 40% | 79% |

REFERENCES

1. C. K. Dorey, G. G. Khouri, L. A. Syniuta, S. A. Curran, J. J. Weiter, *Invest Ophthalmol. Vis. Sci.* 30, 1047-1054 (1989).
2. C. K. Dorey, X. Torres, T. Swart, *Exp. Eye Res.* 50, 1-10 (1990).
3. C. A. Ferguson and S. H. Kidson, *Pigment Cell Res.* 10, 127-138 (1997).
4. M. Miyamoto and T. B. Fitzpatrick, *Science* 126, 449-450 (1957).
5. T. Sarna, *J. Photochem. Photobiol. B.* 12, 215-258 (1992).
6. U. Schraermeyer and K. Heimann, *Pigment Cell Res* 12, 219-236 (1999).
7. Ebadi M, Leuschen M P, el RH, Hamada F M, Rojas P. *Neurochem Int* 29, 159-166 (1996).
8. Rimbach G, Markant A, Pallauf J, Kramer K. *Z Ernährungswiss* 35, 123-142 (1996).
9. Frank R N, Amin R H, Puklin J E. *Am J Ophthalmol* 127, 694-709 (1999).
10. Barrenas M L, Lindgren F. *Br J Audiol* 25, 303-307 (1991).
11. Tate D J, Jr., Miceli M V, Newsome D A. *Free Radic Biol Med* 26, 704-713 (1999).

The invention is claimed is:

1. A pharmaceutical formulation comprising 5,6-dihydroxyindole (DHI) and zinc combined with a pharmaceutically acceptable buffer, diluent or excipient.

* * * * *